United States Patent
Zhen et al.

(10) Patent No.: US 11,195,128 B2
(45) Date of Patent: Dec. 7, 2021

(54) SYSTEMS AND METHODS FOR ESTIMATING HEALTHCARE RESOURCE DEMAND

(71) Applicant: Baidu USA, LLC, Sunnyvale, CA (US)

(72) Inventors: Yi Zhen, San Jose, CA (US);
Hongliang Fei, Sunnyvale, CA (US);
Shulong Tan, Santa Clara, CA (US);
Wei Fan, Sunnyvale, CA (US)

(73) Assignee: Baidu USA LLC, Sunnyvale, CA (US)

( * ) Notice: Subject to any disclaimer, the term of this patent is extended or adjusted under 35 U.S.C. 154(b) by 1158 days.

(21) Appl. No.: 15/226,249

(22) Filed: Aug. 2, 2016

(65) Prior Publication Data

US 2018/0039735 A1    Feb. 8, 2018

(51) Int. Cl.
| | |
|---|---|
| G06Q 10/06 | (2012.01) |
| G16H 40/20 | (2018.01) |
| G16H 10/60 | (2018.01) |
| G16H 15/00 | (2018.01) |
| G16H 50/20 | (2018.01) |

(52) U.S. Cl.
CPC ....... G06Q 10/06315 (2013.01); G16H 10/60 (2018.01); G16H 15/00 (2018.01); G16H 40/20 (2018.01); G16H 50/20 (2018.01)

(58) Field of Classification Search
CPC ........ G16H 10/00; G16H 20/00; G16H 40/00; G16H 40/20; G16H 40/40; G16H 50/00; G16H 50/20; G16H 50/30; G16H 50/50; G16H 50/60; G16H 50/80; G16H 70/00; G16H 70/20; G16H 70/40; G16H 70/60
See application file for complete search history.

(56) References Cited

U.S. PATENT DOCUMENTS

| | | |
|---|---|---|
| 5,528,516 A | 6/1996 | Yemini |
| 8,888,697 B2 | 11/2014 | Bowman |
| 9,734,297 B2 | 8/2017 | Syeda-Mahmood |

(Continued)

FOREIGN PATENT DOCUMENTS

| | | | |
|---|---|---|---|
| CN | 1751309 A | 3/2006 | |
| WO | WO-2011049886 A1 * | 4/2011 | ............. G16H 50/50 |

OTHER PUBLICATIONS

W. Cao and X. Zhang, "Supply Chain Risk Assessment based on Support Vector Machine," Revista Ibérica De Sistemas e Tecnologias De Informação, pp. 310-322, Jul. 10, 2016. (Year: 2016).*

(Continued)

*Primary Examiner* — Gerardo Araque, Jr.
(74) *Attorney, Agent, or Firm* — North Weber & Baugh LLP

(57) ABSTRACT

Presented are systems and methods that allow healthcare providers and governments to infer demand for healthcare resources to ensure effective and timely healthcare services to patients by reducing healthcare supply shortages, emergencies, and healthcare costs. In embodiments, this is accomplished by gathering data from a number of sources to generate labeled records from which entity features and relationships between entities are extracted, correlates, and/or combined with other external healthcare data. In embodiments, this information is used to train a model that predicts healthcare resource demands given a set of input conditions or factors.

20 Claims, 10 Drawing Sheets

(56) References Cited

U.S. PATENT DOCUMENTS

| | | | |
|---|---|---|---|
| 2005/0228815 A1 | 10/2005 | Carus | |
| 2008/0082352 A1* | 4/2008 | Schmidtler | G06Q 50/18 705/2 |
| 2008/0091631 A1 | 4/2008 | Legere | |
| 2009/0216597 A1 | 8/2009 | Cavander | |
| 2009/0216860 A1* | 8/2009 | Li | G06Q 10/067 709/219 |
| 2014/0156806 A1* | 6/2014 | Karpistsenko | G06F 16/25 709/219 |
| 2016/0203264 A1* | 7/2016 | Danner | G06F 19/321 382/128 |
| 2017/0061375 A1* | 3/2017 | Laster | G16H 50/30 |
| 2017/0308613 A1* | 10/2017 | Zhu | G06F 16/9535 |
| 2017/0337481 A1* | 11/2017 | Trouillon | G06N 7/005 |

OTHER PUBLICATIONS

Bengio, "Learning Deep Architectures for AI", Foundations and trends in Machine Learning, Jan. 1, 2009 ;2(1):1-27, (71 pgs).

Wang et al., "Nonnegative matrix factorization: A comprehensive review," Knowledge and Data Engineering, IEEE Transactions on Jun. 2013;25(6):1336-53 (18 pgs).

Cheng et al., "Fused Matrix Factorization with Geographical and Social Influence in Location-Based Social Networks", In Twenty-Sixth AAAI Conference on.

Kohavi, "A Study of Cross-Validation and Bootstrap for Accuracy Estimation and Model Selection", In IJCAI, Aug. 20, 1995 (vol. 14, No. 2, pp. 1137-1145), (16 pgs).

Non-Final Office Action dated Nov. 16, 2018, in U.S. Appl. No. 15/215,393, (43 pgs).

Response filed Feb. 14, 2019, in U.S. Appl. No. 15/215,393, (17 pgs).

Non-Final Office Action dated Sep. 30, 2019, in U.S. Appl. No. 15/215,393, (46 pgs).

Final Office Action dated May 15, 2019, in U.S. Appl. No. 15/215,393, (40 pgs).

Response filed Aug. 15, 2019, in U.S. Appl. No. 15/215,393, (17pgs).

Final Office Action dated May 29, 2020, in U.S. Appl. No. 15/215,393, (41 pgs).

Response filed Jul. 29, 2020, in U.S. Appl. No. 15/215,393, (13 pgs).

Advisory Action dated Aug. 31, 2020, in U.S. Appl. No. 15/215,393, (3 pgs).

Response filed Sep. 29, 2020, in U.S. Appl. No. 15/215,393, (16 pgs).

Non-Final Office Action dated Jan. 6, 2021, in U.S. Appl. No. 15/215,393, (43 pgs).

Response filed Apr. 5, 2021, in U.S. Appl. No. 15/215,393, (14 pgs).

Final Office Action dated Jul. 8, 2021, in U.S. Appl. No. 15/215,393, (43pgs).

Chinese Office Action dated Aug. 11, 2020, in Chinese Application No. 201710184344.6. (15 pgs).

\* cited by examiner

SYSTEMS AND METHODS FOR ESTIMATING HEALTHCARE RESOURCE DEMAND

BACKGROUND

A. Technical Field

The present invention relates to information handling systems and, more particularly, to systems and methods for using information handling systems to estimate demand for healthcare resources.

B. Description of the Related Art

Valuable healthcare resources, such as medical equipment, surgery rooms, medicine, and availability of medical staff needed to provide proper healthcare services to patients, are oftentimes in short supply when lack of foresight makes temporary shortages unavoidable and, in extreme cases, unnecessarily creates life-endangering situations for patients. Currently, there are no tools available to healthcare providers to estimate with reasonable reliability the amount and type of short-term or long-term demand for healthcare resources. Further, seasonal and geographic variations, and even the time of day, make it difficult for healthcare providers to obtain meaningful estimates of levels of demand for healthcare resources at any given time. Furthermore, variables, such as cost and policy decisions, outbreak of diseases, and the like, exacerbate the difficulty in forecasting actual demand.

Therefore, it would be desirable to have tools that allow healthcare providers and governments to infer, with reasonable accuracy, demand for healthcare resources, so as to ensure effective and timely healthcare services to benefit patients by reducing healthcare supply shortages and emergencies resulting therefrom and, ultimately reduce healthcare costs.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

Figure 1:
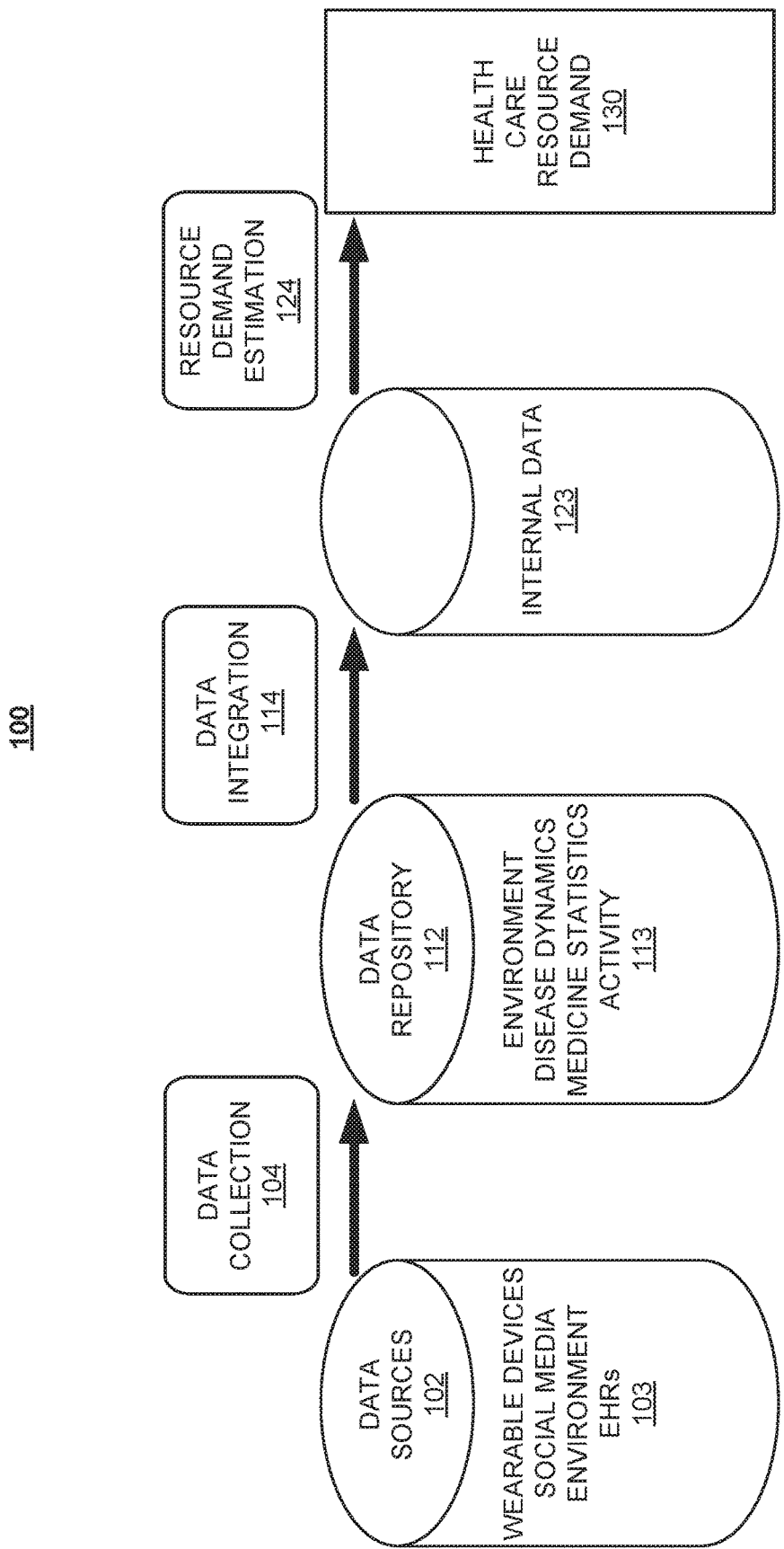
FIG. 1 illustrates an exemplary system for generating healthcare resource demand data according to various embodiments of the present disclosure.

In the following description, for purposes of explanation, specific details are set forth in order to provide an understanding of the invention. It will be apparent, however, to one skilled in the art that the invention can be practiced without these details. Furthermore, one skilled in the art will recognize that embodiments of the present invention, described below, may be implemented in a variety of ways, such as a process, an apparatus, a system, a device, or a method on a tangible computer-readable medium.

Components, or modules, shown in diagrams are illustrative of exemplary embodiments of the invention and are meant to avoid obscuring the invention. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components. Components may be implemented in software, hardware, or a combination thereof.

Furthermore, connections between components or systems within the figures are not intended to be limited to direct connections. Rather, data between these components may be modified, re-formatted, or otherwise changed by intermediary components. Also, additional or fewer connections may be used. It shall also be noted that the terms "coupled," "connected," or "communicatively coupled" shall be understood to include direct connections, indirect connections through one or more intermediary devices, and wireless connections.

Reference in the specification to "one embodiment," "preferred embodiment," "an embodiment," or "embodiments" means that a particular feature, structure, characteristic, or function described in connection with the embodiment is included in at least one embodiment of the invention and may be in more than one embodiment. Also, the appearances of the above-noted phrases in various places in the specification are not necessarily all referring to the same embodiment or embodiments.

The use of certain terms in various places in the specification is for illustration and should not be construed as limiting. A service, function, or resource is not limited to a single service, function, or resource; usage of these terms may refer to a grouping of related services, functions, or resources, which may be distributed or aggregated. Furthermore, the use of memory, database, information base, data store, tables, hardware, and the like may be used herein to refer to system component or components into which information may be entered or otherwise recorded.

Furthermore, it shall be noted that: (1) certain steps may optionally be performed; (2) steps may not be limited to the specific order set forth herein; (3) certain steps may be performed in different orders; and (4) certain steps may be done concurrently.

FIG. 1 illustrates an exemplary system for generating healthcare resource demand data according to various embodiments of the present disclosure. System 100 comprises data sources 102, data collector 104, data repository 112, data integrator 114, internal data 123, and resource demand estimator 124. Data sources 102 may be semi-structured sources of data, such as wearable devices, social media, environmental data, and electronic healthcare records (EHRs). Data repository 112 and internal data 123 may be any storage medium or media, such as non-volatile memory.

In embodiments, data collector 104 gathers data from one or more data sources 102 and transforms the collected data into a new representation, for example, by generating labeled records 113 that may be stored in data repository 112. In embodiments, data integrator 114 receives labeled records 113 from data collector 104 and/or data repository 112, extracts entity features and relationships between entities, and uses matrix manipulation methods to correlate and combine the data with internal and/or external healthcare data to obtain integrated records.

Examples of systems and methods for parsing and extracting entities, e.g., medical entities, may be found in co-pending and commonly-owned U.S. patent application Ser. No. 15/215,393, filed on 20 Jul. 2016, entitled "SYSTEMS AND METHODS FOR FINER-GRAINED MEDICAL ENTITY EXTRACTION," and listing Hongliang Fei, Shulong Tan, Yi Zhen, Erheng Zhong, Chaochun Liu, Dawen Zhou, and Wei Fan as inventors, which patent document is incorporated by reference herein in its entirety and for all purposes.

The integrated records may be used as input to resource demand estimation model 124 that, in embodiments, is trained to perform resource demand estimation to generate and output a healthcare resource demand estimate 130. Each of data collector 104, data integrator 114, and resource demand estimator 124 are discussed in more detail with respect to FIG. 3-8.

Figure 2:
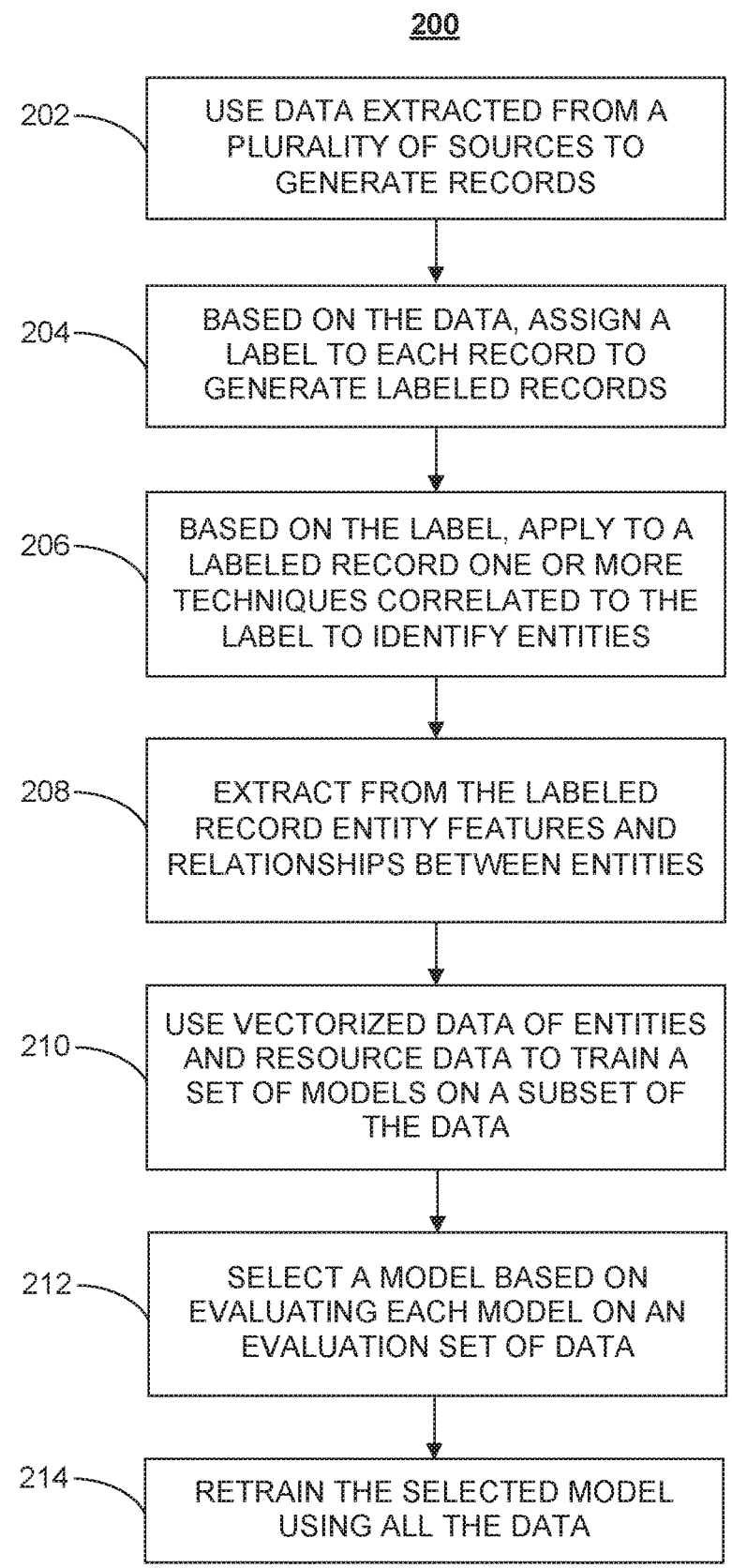
FIG. 2 illustrates a method for generating healthcare resource demand data according to various embodiments of the present disclosure.

FIG. 2 illustrates a method for generating healthcare resource demand data according to various embodiments of the present disclosure. In embodiments, a process 200 for generating healthcare resource demand data begins at step 202 by generating records from data extracted from one or more sources. In embodiments, the data may be from unstructured, semi-structured, and/or structured data sources.

In embodiments, at step 204, based on the extracted data, a label is assigned to each record to generate a number of labeled records. In embodiments, a plurality of labels may be used, such as environment, disease dynamics, medicine statistics, and activity, although different and/or other labels may be used.

In embodiments, at step 206, based on the label, one or more techniques correlated to the label is assigned to each labeled record to identify entities within the records. In embodiments, the techniques such as machine learning processes, label-specific dictionaries, etc., may be used to extract entities.

In embodiments, at step 208, entity features and relationships between the entities extracted from the labeled records are used to generate vectorized representations of entities.

In embodiments, at step 210, vectorized data of entities and internal or external healthcare data is used to train a set of models on a subset of the data.

In embodiments, at step 212, based on an evaluation of each model using an evaluation set of data, the preferred model is selected.

Finally, in embodiments, at step 214, the preferred model is retrained by using more than the evaluation set of data, e.g., all the data.

Figure 3:
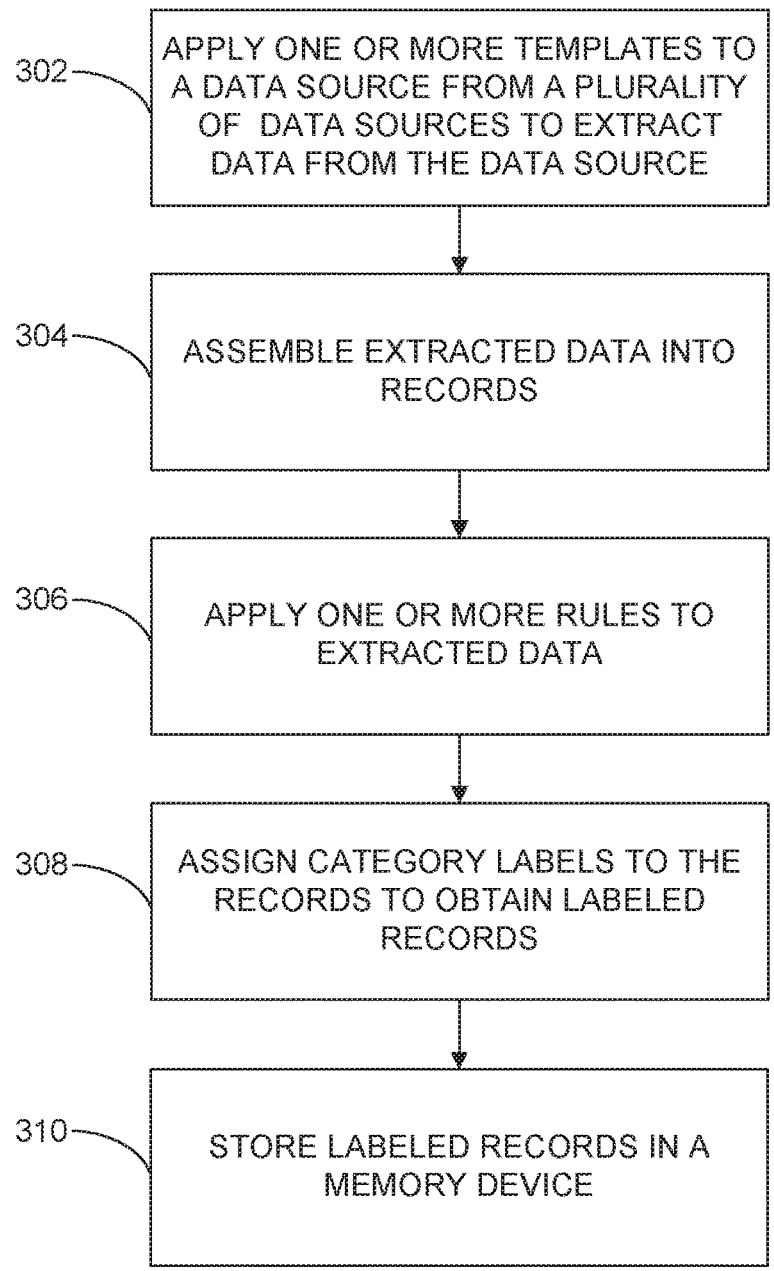
FIG. 3 illustrates a method for collecting multi-source data according to various embodiments of the present disclosure.

FIG. 3 illustrates a method for collecting data from a plurality of sources according to various embodiments of the present disclosure. Examples of data sources include websites, social media, search logs from a search engine, electronic health records, wearable devices, etc. In embodiments, the process for collecting data comprises applying (302) one or more templates to a data source from a plurality of data sources to extract data from the source. For example, one or more templates, such as a data extraction template that is matched to a specific website or webpage format, Application Programming Interfaces (APIs) for a site or device, etc., may be applied to data gathered from a source. Templates may be specific to each source and depend on a structure of the source that may already exist. In embodiments, each template may use a set of rules that are tailored to extract data from a data source based on one or more keywords from a dictionary. In embodiments, one or more user-designed or learned rules may be applied to the data as part of the extraction process.

In embodiments, a template may be a set of rules and keywords. For example, a template for search logs may include rules for extracting human activities: extract logs matching "human name or ID+activity names". A template for web pages may include rules for extracting disease and symptom relations: extract paragraphs matching "[disease name] may have the following symptoms: [symptom name 1, symptom name2, . . . ]". For yet another example, the following template may be used to extract weather information about a city from a web page: <html><title>weather</title>+[weather content]</html>. One skilled in the art shall recognize other templates may be created and used and such fall within the scope of the current disclosure.

In embodiments, the extracted data is assembled (304) into a number of records. In embodiments, any portion of data (e.g., words, sentences, paragraphs, sections, etc.) may be formed into a record. For example, in embodiments, a field or section of a data source or data obtained using an API from a data source may form a record. For yet another example, a record may be raw text paragraphs and some numeric values, such as temperature. In embodiments, there are no general rules for formatting the extracted data into records; rather, the records may be simply extracted data plus a timestamp and may include some other specific values (such as zip code and city name). In embodiments, a portion of data may be combined with other data to generate a record. It is understood that data from one or more data sources may be combined to generate a record or add data to an existing record.

In embodiments, one or more rules or processes (306) are applied to the extracted data. In embodiments, the one or more rules may include: (1) filling in at least one or more missing values; (2) gauging the reliability of source; (3) applying privacy settings to convert personally identifiable information into non-personally identifiably information; (4) performing data alignment in which data from different sources may be linked via one or more pieces of information; and (5) applying one or more association rules for identify different connections or associations in data.

For example, in embodiments, a missing value imputation may be performed to add one or more values not present in a record. Values may be missing for a number of reasons, such as because at a certain time a data point has not been recorded. In embodiments, values may be added based on historic data, interpolation, extrapolation, correlation to other records, etc. For example, assuming that dates are identified for which no data about weather conditions are available, then data for the missing date may be interpolated or extrapolated from values for days preceding the missing date or may be inferred by looking at weather records for nearby locations. In embodiments, where a value has not been recorded and no reasonable value can be obtained or where a value exceeds a threshold value or falls outside of a permissible data range, the missing or improper data point may be labeled as out-of-range.

In embodiments, a data source may be gauged as to its reliability. For example, in embodiments, if the number of missing data fields or values for a data source exceeds a threshold level, then that source may be noted as being less reliable or data from the source may be altogether discarded.

In embodiments, data privacy control is enabled, for example, by normalizing data to protect personal or private data of patients prior to releasing results. This may be accomplished by removing, modifying, or hiding information, such as a user or device identification, e.g., by using a hash table that transforms to be protected data into some relatively less discoverable and, thus, safer format. In embodiments, data reliability is improved by adding a location verification to the data received from one or more semi-structured data sources, for example, by matching zip codes with corresponding town names.

In embodiments, data alignment may be performed using one or more field from one source to align information from another source. For example, a data entry into a website or social media site (e.g., "My allergies are really bad this morning!") that includes a timestamp can be used to correlate with the weather conditions (such as pollen levels) at that time. In embodiments, pre-selected fields may be used for alignment. For example, a social media site's user account might include the following fields: a user/patient identifier, a gender, a city, and a zip code. A rule may exist that for each record, the city or zip code field may be correlated to environment records (e.g., temperature, air quality, humidity, etc.) for that city or zip code to create new records, which may later be assigned a label.

In embodiments, data from one of more sources may be used to derive association rules that may be used to find and/or replace missing values in a record. As one example, assuming that data collected from a number of data sources shows that 60% of males between the ages of 40-45 are identified as smokers, then this information may be used to learn a rule that would aid in calculating a missing value for a 42-year-old male for whom the record comprises no data point regarding smoking to populate an otherwise empty field "smoking" with a "yes." One of skill in the art will appreciate that association rule learning may be supervised or unsupervised.

In embodiments, category labels, such as, e.g., disease, activity, environment, and medicine are assigned (308) to records to obtain labeled records. In embodiments, records may be categorized based on a comparison of data received one or more data sources and/or data derived therefrom. As with data collection and data extraction, the assigning of category labels, at step 308, may be based on keywords searches, knowledge of the source and/or field from which the record was obtained, and/or using one or more learned models.

It is understood that labels may be assigned for any number of categories. It is noted that the predetermined keywords may or may not overlap with category labels, such that keywords in a sub-category, a related category, or a similar sounding category may be assigned to the same category. For example, the term medication in one source may be assigned to the same "medicine" category as the term "Aspirin" occurring in another source.

Finally, the labeled records may be stored (310) in a datastore.

One skilled in the art will appreciate that any of a number of learning-based methods may be used to extract data, assign labels, or both without deviating from the scope of the present disclosure.

Figure 4:
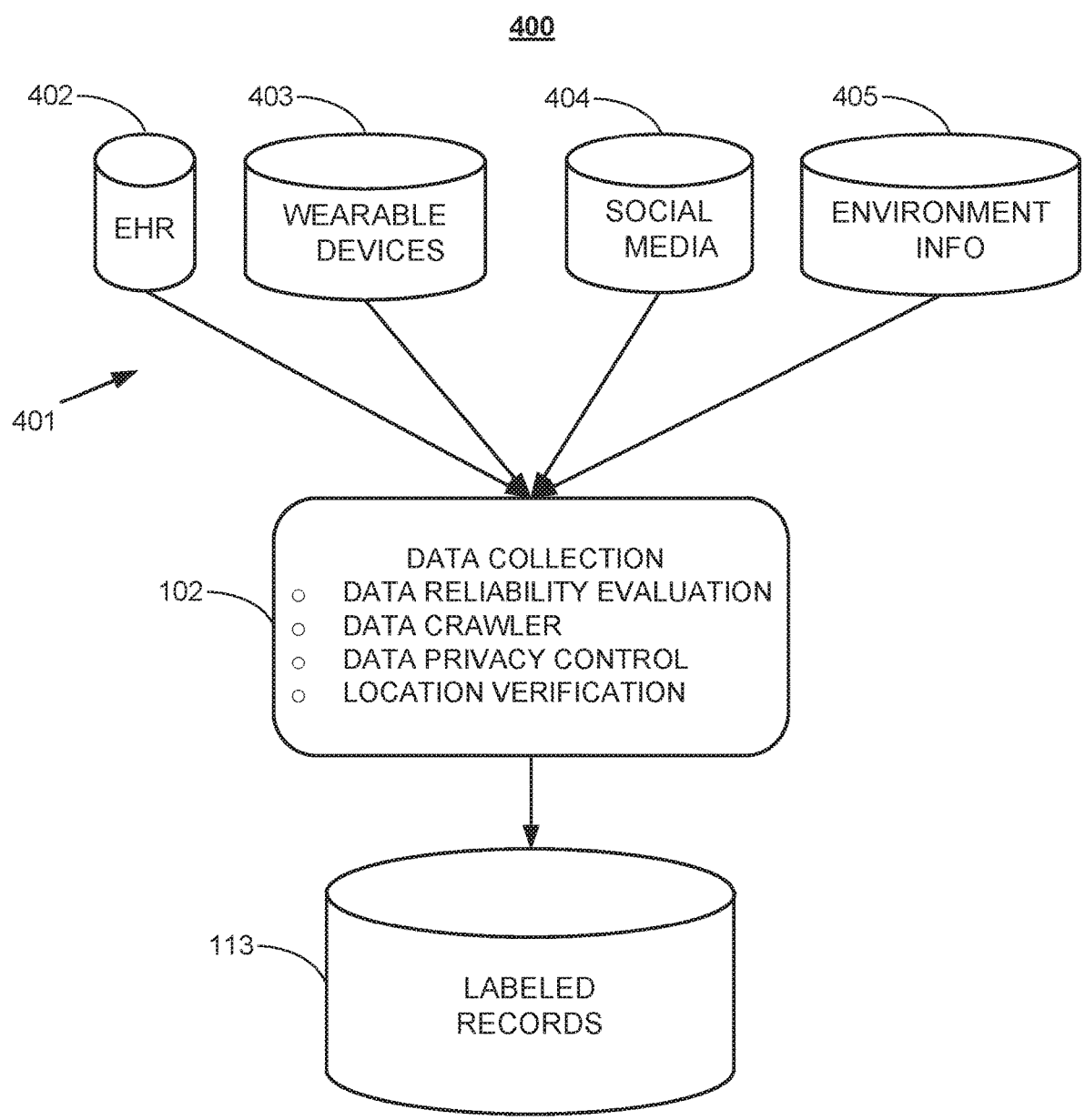
FIG. 4 illustrates a system for collecting multi-source data according to various embodiments of the present disclosure.

FIG. 4 illustrates a system for collecting multi-source data according to various embodiments of the present disclosure. System 400 comprises unstructured, structured, and/or semi-structured data sources 401 and data collector 102 that outputs labeled records 113. In embodiments, data collector 102 is coupled to extract data from the data sources 401, such as, for example, electronic healthcare records 402, wearable devices 403, social media 404, and environmental data sources 405, and assemble the extracted data into labeled records 113.

In embodiments, the data collector 102 comprises a data crawler (not shown) that applies a source-specific templates or techniques to data sources to extract data, such as described above with respect to step 302 in FIG. 3. In embodiments, the data collector 102 (which may be a function of the data crawler) and assembles data into a number of records, such as according to step 304 in FIG. 3.

In embodiments, the data collector 102 identifies values that are not present in a record and, prior to generating output 113, supplies the values. In embodiments, the data collector 102 may supply missing values as described above with reference to step 308 in FIG. 3.

In embodiments, the data collector 102 assigns category labels to records to obtain labeled records, as described above with respect to step 308 in FIG. 3. In embodiments, the data collector 102 may use the categorized data to generate a labeled record according to a category (e.g., disease) or to add the categorized data to an existing record. For example, the timestamp on some patient-generated data retrieved from social media source 404 may be used to find related environmental data, e.g., weather data describing a weather condition matching the timestamp. This information may then be added to a record or used to generate a new record.

Finally, in embodiments, the labeled records may be stored in data repository 112.

Figure 5:
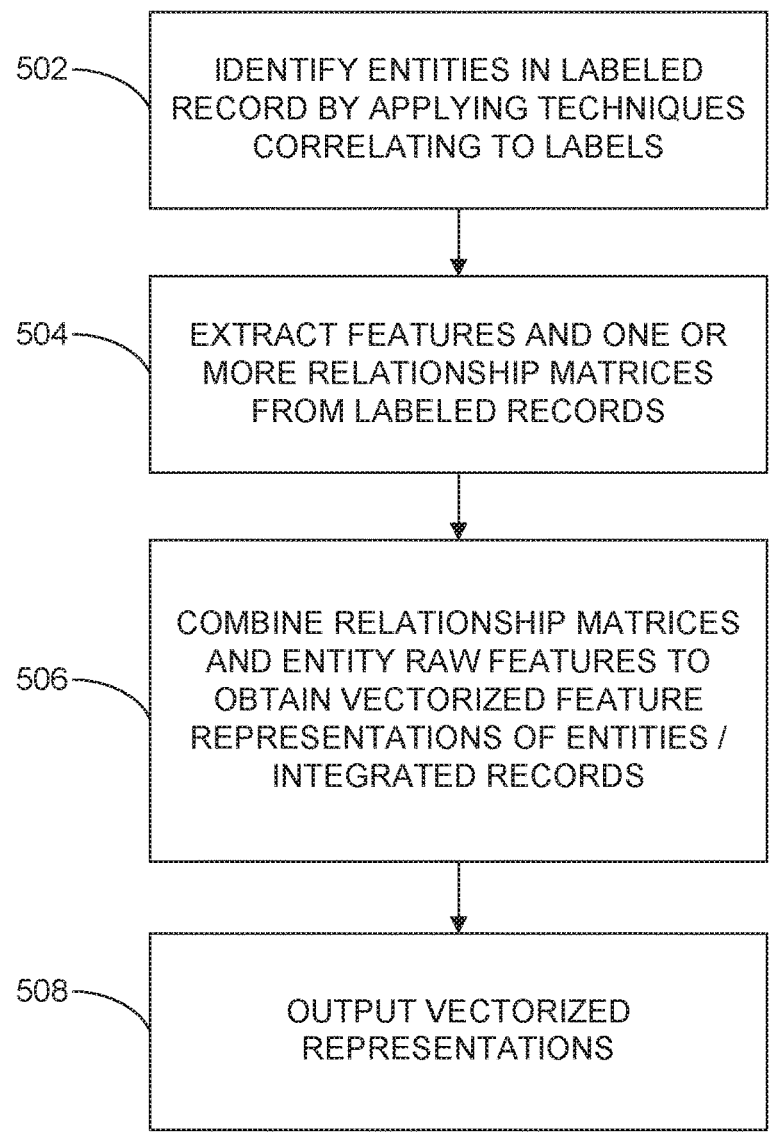
FIG. 5 illustrates a method for integrating data according to various embodiments of the present disclosure.

FIG. 5 illustrates a method for integrating data according to various embodiments of the present disclosure. In embodiments, the integration process commences by identifying (502) entities in labeled records, which may be obtained from a data repository. In embodiments, labeled records may be numerical (such as a bag of words) or plain text data. In embodiments, one or more techniques for extracting entities may be correlated to the label of a record. For example, in embodiments, a specific dictionary correlated to a label may be used for keyword search. Similarly, in embodiments, learned models may be used to extract entities based upon label. In embodiments, a learning-based model or models may be used together with a dictionary-based model or models to find as many entities as possible.

In embodiments, one or more knowledge transfer methods, in which one or more machine learning-based models for different labels can transfer knowledge between each other, may be employed to increase or improve learning. For example, knowledge from label A may be used to learn a model for label B. In embodiments, the identification of entities may be performed by employing one or more deep learning methods that are trained to identify entities in records.

In embodiments, features and relationships between entities may also be extracted (504) from the labeled records. In embodiments, one or more correlations analyses may be used to help identify correlations relationships or features between entities. In embodiments, data alignment may be performed using one or more field from one record to align information from another record to create relationships. For example, a record that contains a linking piece of information (such as an entity, date, location, etc.) may be used to link to another record to establish a relationship. In embodiments, pre-selected fields may be used for alignment.

Consider, by way of illustration, the efficacy relationship between different treatments or different medicines and a disease may be extracted. For example, a record about treatments for various diseases may be used to extract data about the various treatments for a particular disease. In embodiments, these relationships may be represented in one or more matrices that indicate relationships between the entities; or, relationships may be extracted from relationship matrices in which each entry represents a relationship between entities.

In embodiments, the fields in a record may undergo format conversion. For example, fields may be treated or converted into integers or values (e.g., using a bag of words or other representation) to index or replace raw text with an index that can be placed into a vector such that it can be mathematically manipulated to perform operations and analysis between fields and/or to form a vector representation of features.

In embodiments, relationship matrices, entity, and entity raw features are combined or used (506) to form rich representations. For example, in embodiments, matrix decomposition, machine learning, or other processes known to those skilled in the art may be used to obtain vectorized feature representations of entities and/or integrated records. In embodiments, a deep learning method may be used to combine vectorized feature representations that are associated with one or more records with resources data (e.g., hospital resources data) to generate integrated records.

In embodiments, a vectorized feature representation may be, for example, an n-dimensional numerical vector that comprises elements that each has a value. In embodiments, each entity (e.g., a disease) in a vectorized feature representation may be represented as a single vector.

At step 508, the vectorized representations of integrated records are output for further processing, for example, to train a set of models (e.g., an RNN model and a logistic regression model) to estimate a health resources demand.

Figure 6:
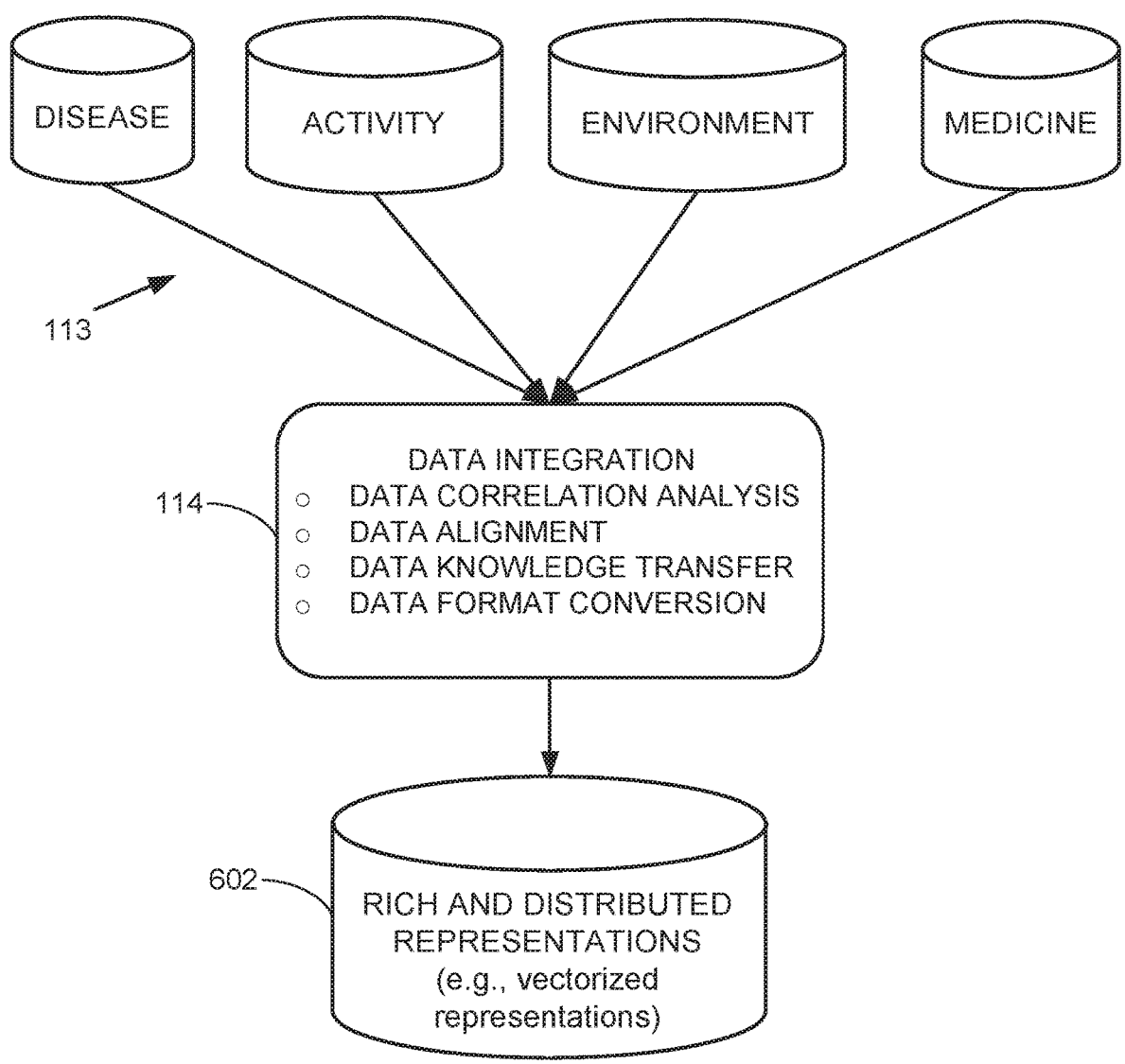
FIG. 6 illustrates a system for integrating data according to various embodiments of the present disclosure.

FIG. 6 illustrates a system for large scale integration of multi-source data according to various embodiments of the present disclosure. System 600 comprises labeled records 113, data integrator 114, and output 602. Data integrator 114 is coupled to receive labeled records 113 from data repository (not shown) to generate rich and distributed representations 602.

In embodiments, the data integrator 114 obtains, e.g., from a data repository comprising labeled records 113 one or more entities that each are associated with at least one labeled record 113. In embodiments, based on the entities, data integrator 114 extracts features and relationships, such as described according to step 504 in FIG. 5.

In embodiments, the data integrator 114 may perform one or more data correlations, one or more data alignment processes, one or more knowledge transfers, and/or one or more data format conversions, such as those previously discussed to aid in the processes of entity and feature extraction and forming representations.

In embodiments, the extracted entity features, which may include relationship matrices and raw features of entities, are converted to rich representations, such as vectors. In embodiments, matrix decomposition, machine learning, and/or other processes may be used to convert the representations into the representations.

In embodiments, vectorized representations for each entity are rich and distributed representations 602 that are input for use in training one or more models (not shown), such as an RNN model or a logistic regression model, that are trained to estimate a health resources demand as discussed next.

Figure 7:
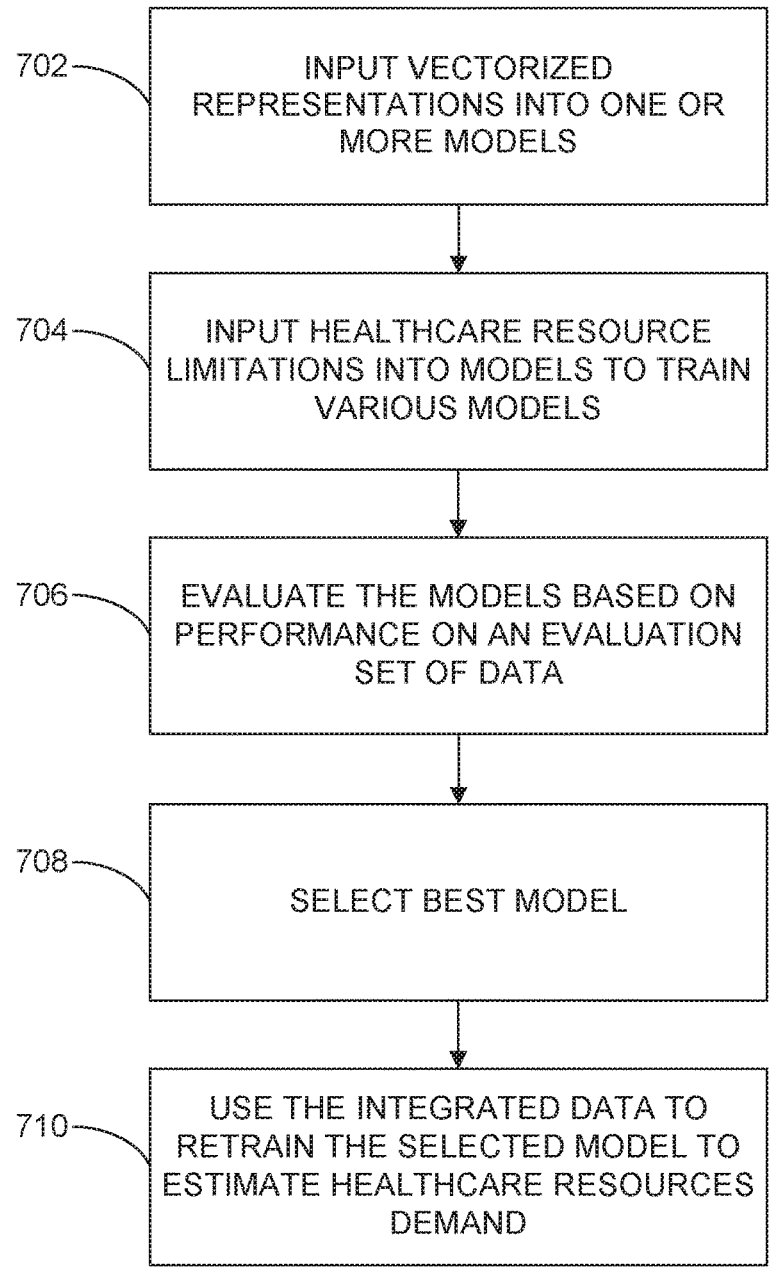
FIG. 7 illustrates a method for obtaining a model for estimating resource demand according to various embodiments of the present disclosure.

FIG. 7 illustrates a method for obtaining a model for estimating resource demand according to various embodiments of the present disclosure. In embodiments, the method for estimating resource demand begins when vectorized representations of integrated records are used to (702) to train one or more models.

In embodiments, healthcare resource limitations and knowledge, such as usage information that is based on healthcare resources data, are input (704) to the one or more models. Hospital logistics examples may include such things as the number of surgery rooms that are available during a specific time period, budgets (e.g., a total budget is $1 million for a radiology department), etc. Healthcare knowledge examples may include such information as length of time a certain procedure takes from preparation to finish, materials used, and amount of staff. In embodiments, the healthcare knowledge may be text rules, which may be translated or converted into one or more equations (e.g., EndTime−StartTime<=3 days).

In embodiments, the models are evaluated (706), for example, based on performance on an evaluation set of data.

In embodiments, the best model is selected (708) based on one or more performance criteria, for example, being the model closest to a set of ground truth data.

In embodiments, integrated data is used to retrain (710) the selected model to estimate resource demand, e.g., healthcare resources demand.

Figure 8:
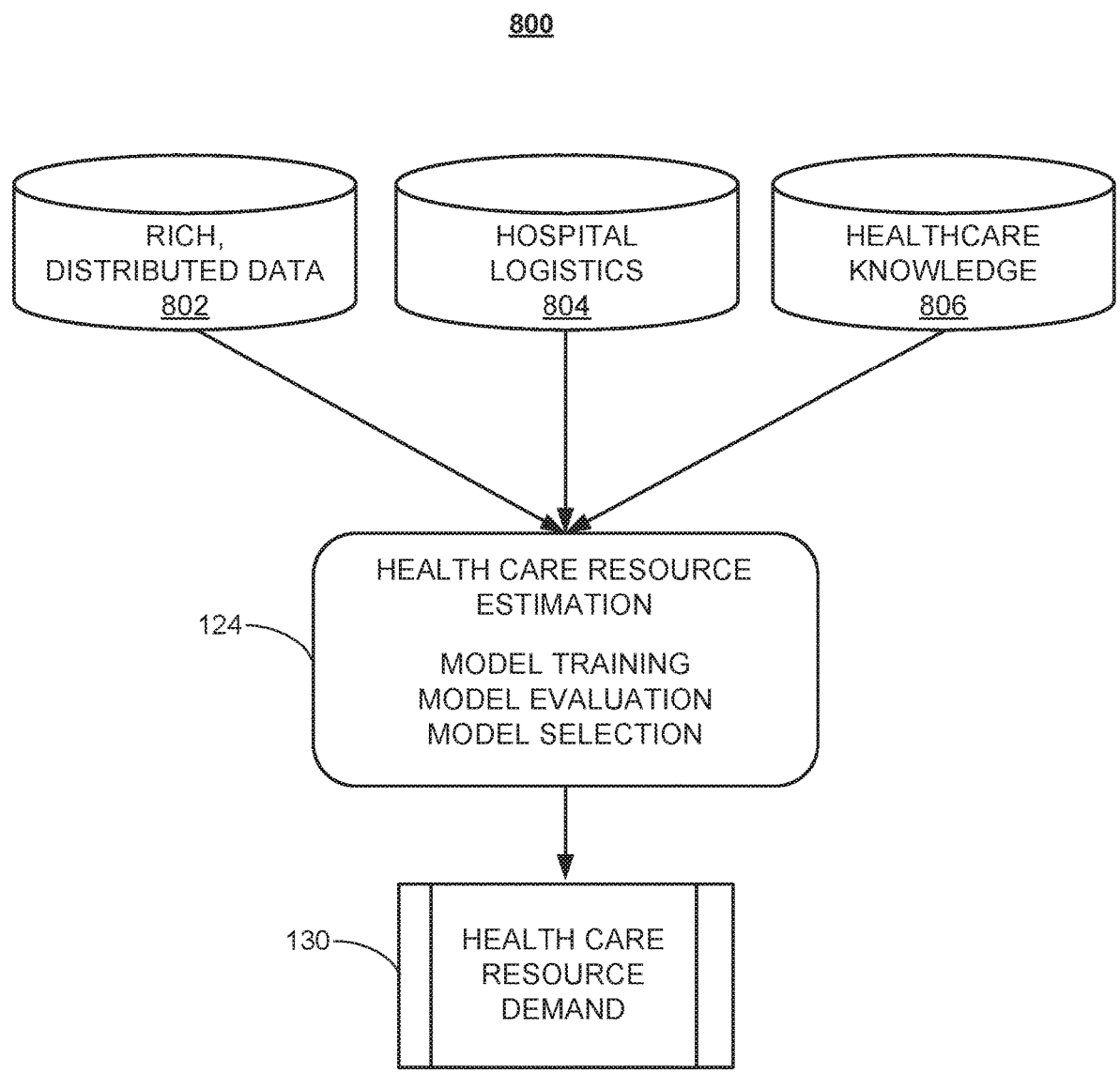
FIG. 8 illustrates a system for training and selecting a model to estimate resource demand according to various embodiments of the present disclosure.

FIG. 8 illustrates a system for training and selecting a model to estimate resource demand according to various embodiments of the present disclosure.

System 800 comprises resource estimator 124 that is coupled to receive rich and distributed data 802, hospital logistics information 804, and healthcare knowledge data 806 from which it generates healthcare resource demand 130. Hospital logistics information 804 may include, for example, the limitations or resources available (e.g., the number of surgery rooms that are available during a specific time period, a budget for a specific department, etc.), staffing, and other such data. Healthcare knowledge data 806 may include, for example, the expected duration and supplies required for a medical procedure. These sets of information may be rule-based and may include present and historical data information related to hospital logistics, financial data, and any other factors.

In embodiments, resource estimator 124 receives vectorized representations 802, hospital logistics data 804, and healthcare resource data 806 as inputs. In embodiments, the representations may be input data of the models, and the latter two sets of data may be organized as constraints for the models to be trained. It shall be noted that other data may also be supplied. In embodiments, based on this information, resource estimator 124 trains a supervised, semi-supervised, unsupervised learning model, or combinations thereof to estimate healthcare resource demand 130.

In embodiments, the resource estimator 124 validates each model and, based on evaluation results, selects the best performing model. For example, in embodiments, the models may be trained using ground truth data, in which a subset of the data is reserved as an evaluation set. The trained models may each be evaluated using the evaluation set of data, and based on performance, a best model may be selected. In embodiments, the selected model may be retrain using all available ground truth data.

Figure 9:
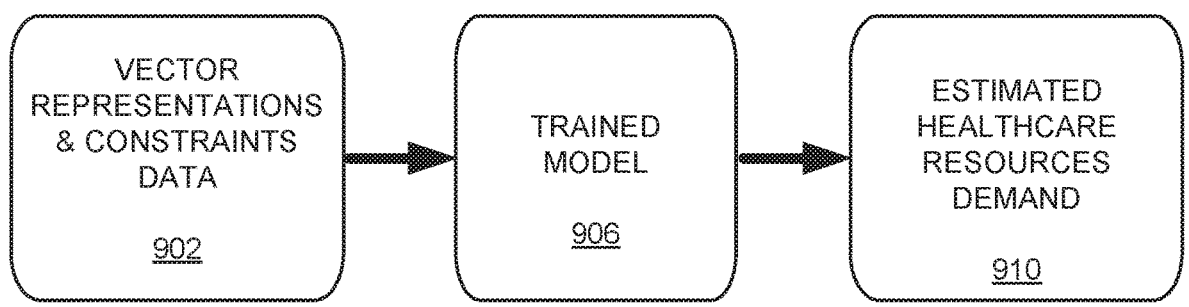
FIG. 9 illustrates a method for estimating resource demand according to various embodiments of the present disclosure.

FIG. 9 illustrates a method for estimating resource demand according to various embodiments of the present disclosure. The process for estimating a resource demand begins at step 902 when vector representations and external data, such as, for example, hospital logistics data and healthcare knowledge are input into a trained model. In embodiments, external data may be organized as constraints for the model. For example, in embodiments, the inputs are the entities involved and one or more constraint equations, which have been translated from specific limitations and knowledge. In embodiments, the model may have been selected from a plurality of models.

At step 906, the trained model processes the input data and outputs, at step 910, an estimated healthcare resources demand.

Figure 10:
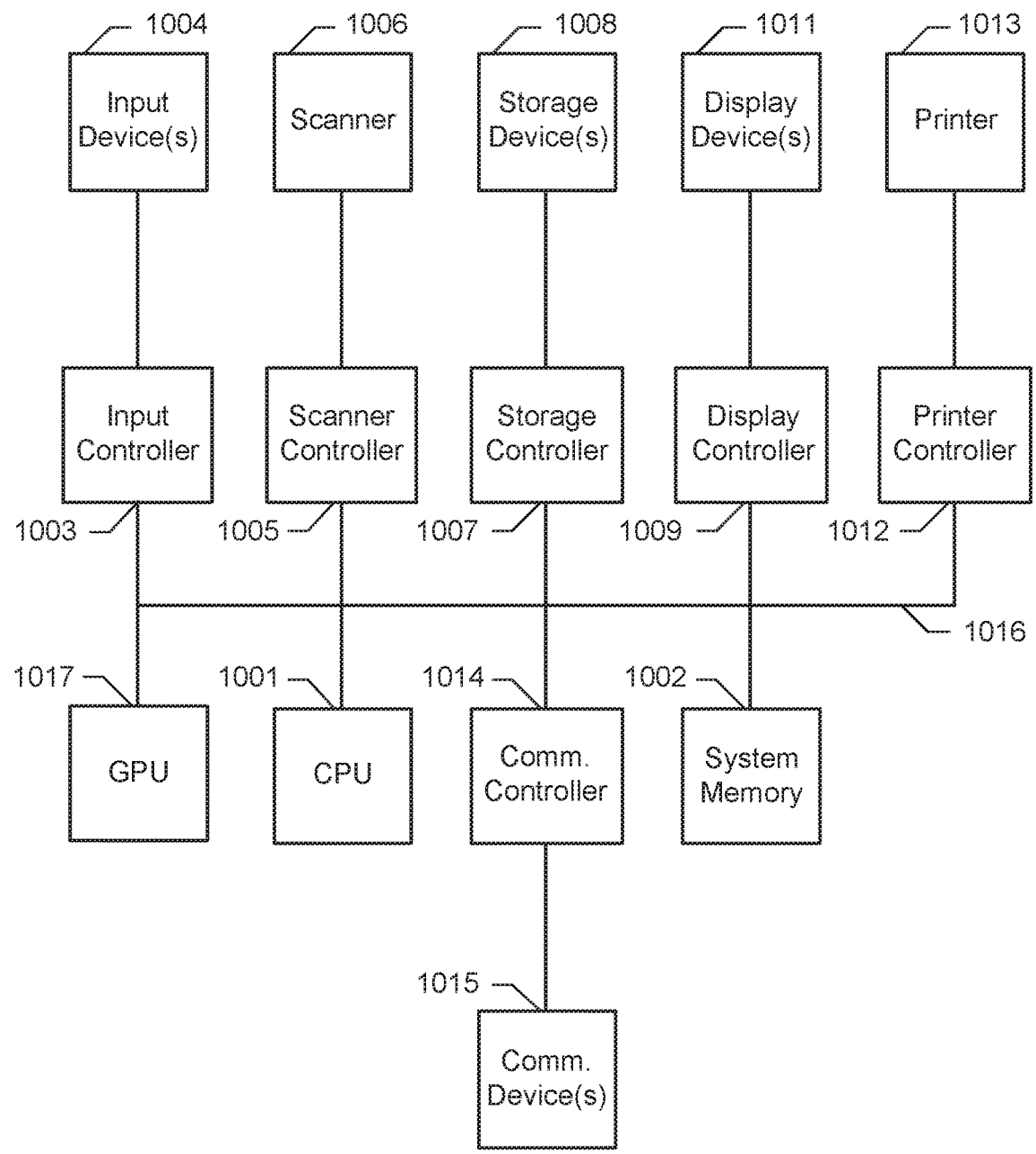
FIG. 10 depicts a simplified block diagram of a computing system according to various embodiments of the present invention.

FIG. 10 depicts a simplified block diagram of a computing system for generating healthcare resource demand data, according to various embodiments of the present invention. It will be understood that the functionalities shown for system 1000 may operate to support various embodiments of an information handling system—although it shall be understood that an information handling system may be differently configured and include different components. As illustrated in FIG. 10, system 1000 includes a central processing unit (CPU) 1001 that provides computing resources and controls the computer. CPU 1001 may be implemented with a microprocessor or the like, and may also include a graphics processor and/or a floating point coprocessor for mathematical computations. System 1000 may also include a system memory 1002, which may be in the form of random-access memory (RAM) and read-only memory (ROM).

A number of controllers and peripheral devices may also be provided, as shown in FIG. 10. An input controller 1003 represents an interface to various input device(s) 1004, such as a keyboard, mouse, or stylus. There may also be a scanner controller 1005, which communicates with a scanner 1006. System 1000 may also include a storage controller 1007 for interfacing with one or more storage devices 1008 each of which includes a storage medium such as magnetic tape or disk, or an optical medium that might be used to record programs of instructions for operating systems, utilities and applications which may include embodiments of programs that implement various aspects of the present invention. Storage device(s) 1008 may also be used to store processed data or data to be processed in accordance with the invention. System 1000 may also include a display controller 1009 for providing an interface to a display device 1011, which may be a cathode ray tube (CRT), a thin film transistor (TFT) display, or other type of display. The computing system 1000 may also include a printer controller 1012 for communicating with a printer 1013. A communications controller 1014 may interface with one or more communication devices 1015, which enables system 1000 to connect to remote devices through any of a variety of networks including the Internet, an Ethernet cloud, a Fibre Channel over Ethernet (FCoE)/Data Center Bridging (DCB) cloud, a local area network (LAN), a wide area network (WAN), a storage area network (SAN) or through any suitable electromagnetic carrier signals including infrared signals.

In the illustrated system, all major system components may connect to a bus 1016, which may represent more than one physical bus. However, various system components may or may not be in physical proximity to one another. For example, input data and/or output data may be remotely transmitted from one physical location to another. In addition, programs that implement various aspects of this invention may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

Embodiments of the present invention may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to create non-transitory implementations, such as write program code (i.e., software) and/or to fabricate circuits (i.e., hardware) to perform the processing required.

It shall be noted that embodiments of the present invention may further relate to computer products with a non-transitory/tangible computer-readable medium that have computer code thereon for performing various computer-implemented operations. The media and computer code may be those specially designed and constructed for the purposes of the present invention, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present invention may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

One skilled in the art will recognize no computing system or programming language is critical to the practice of the present invention. One skilled in the art will also recognize that a number of the elements described above may be physically and/or functionally separated into sub-modules or combined together.

It shall be noted that elements of the claims, below, may be arranged differently including having multiple dependencies, configurations, and combinations. For example, in embodiments, the subject matter of various claims may be combined with other claims.

It will be appreciated to those skilled in the art that the examples and embodiments herein are exemplary and not limiting to the scope of the present invention. It is intended that all permutations, enhancements, equivalents, combinations, and improvements thereto that are apparent to those skilled in the art upon a reading of the current document are included within the true spirit and scope of the present invention.

What is claimed is:

1. A method for estimating a resource demand, the method comprising:
    one or more processors performing the steps comprising:
        extracting data from a plurality of sources by applying a set of one or more rules correlated to at least some of the sources from the plurality of sources by performing one or more steps comprising:
            applying a template that is source specific for extracting data from the source, wherein the template is source specific by being matched to a data format for a website, webpage, datastore, or device, or is matched to one or more Application Programming Interfaces (APIs) for a website, webpage, datastore, or device;
            applying one or more keywords from a list of keywords to identify corresponding data in the source; and
            applying a learned model to the source, wherein the set of one or more rules represent the learned model;
        using at least some of the extracted data to generate records;
        assigning one or more labels to each record based upon a category associated with the record or corresponding to at least some of the data contained in the record to obtain labeled records;
        identifying one or more entities within each labeled record by applying to a labeled record one or more techniques correlating to that label for identifying an entity or entities;
        generating, from the labeled records, entity features and relationships between two or more entities by correlating data from the labeled records that are related to the two or more entities that are identified in labeled records;
        for each entity of a set of entities identified in the labeled records, using (1) matrix manipulation on a matrix that represents entity features and relationships between two or more entities, (2) a machine learning model that receives one or more entity features that are related with one or more features of one or more other entities and outputs the vectorized representation of the entity features and relationships, or (3) both to convert the entity features and relationships between two or more entities into the vectorized representation of the entity;
        using vectorized representations of entities and resource data to train a set of models using a first set of data;
        evaluating each trained model of the set of models using an evaluation set of data; and
        selecting a trained model from the set of models based on evaluations.

2. The method of claim 1, further comprising retraining the selected trained model.

3. The method of claim 1, wherein the step of extracting the data further comprises:
    assessing a reliability factor for a source; and
    in response to determining a low reliability factor for the source, excluding data from that source to improve data reliability.

4. The method of claim 1, wherein the step of generating entity features and relationships comprises combining data from at least two of the plurality of sources.

5. The method of claim 1, wherein the step of generating entity features and relationships comprises at least one of correlating or aligning data from two or more of the plurality of sources.

6. The method of claim 1, wherein the resource data is represented as one or more rule-based limitations, which are used as constraints in the model.

7. The method of claim 1, wherein the step of extracting the data further comprises converting personally identifiable information into non-personally identifiable information to preserve data privacy.

8. The method of claim 1, wherein an entry in the matrix represents a relationship between entities.

9. The method of claim 8, further comprising applying matrix decomposition or matrix factorization to one or more matrices to generate a vectorized representation for an entity.

10. A non-transitory computer-readable medium or media comprising one or more sequences of instructions which, when executed by at least one processor, causes steps to be performed comprising:
    extracting data from a plurality of sources by applying a set of one or more rules correlated to at least some of the sources from the plurality of sources by performing one or more steps comprising:
        applying a template that is source specific for extracting data from the source, wherein the template is source specific by being matched to a data format for a website, webpage, datastore, or device, or is matched to one or more Application Programming Interfaces (APIs) for a website, webpage, datastore, or device;
        applying one or more keywords from a list of keywords to identify corresponding data in the source; and
        applying a learned model to the source, wherein the set of one or more rules represent the learned model;
    using at least some of the extracted data to generate records;
    assigning one or more labels to each record based upon a category associated with the record or corresponding to at least some of the data contained in the record to obtain labeled records;
    identifying one or more entities within each labeled record by applying to a labeled record one or more techniques correlating to that label for identifying an entity or entities;

generating, from the labeled records, entity features and relationships between two or more entities by correlating data from the labeled records that are related to the two or more entities that are identified in labeled records;

for each entity of a set of entities identified in the labeled records, using (1) matrix manipulation on a matrix that represents entity features and relationships between two or more entities, (2) a machine learning model that receives one or more entity features that are related with one or more features of one or more other entities and outputs the vectorized representation of the entity features and relationships, or (3) both to convert the entity features and relationships between two or more entities into the vectorized representation of the entity;

using vectorized representations of entities and resource data to train a set of models using a first set of data;

evaluating each trained model of the set of models using an evaluation set of data; and selecting a trained model from the set of models based on evaluations.

11. The non-transitory computer-readable medium or media of claim 10, wherein the step of generating entity features and relationships comprises at least one of correlating or aligning data from two or more of the plurality of sources.

12. The non-transitory computer-readable medium or media of claim 10, wherein the resource data is represented as one or more rule-based limitations, which are used as constraints in the model.

13. The non-transitory computer-readable medium or media of claim 10, further comprising one or more sequences of instructions which, when executed by at least one processor, causes steps to be performed comprising:
retraining the selected trained model.

14. The non-transitory computer-readable medium or media of claim 10, wherein the step of extracting the data further comprises:
assessing a reliability factor for a source; and
in response to determining a low reliability factor for the source, excluding data from that source to improve data reliability.

15. The non-transitory computer-readable medium or media of claim 10, wherein the step of generating entity features and relationships comprises combining data from at least two of the plurality of sources.

16. A system comprising:
one or more processors; and
a non-transitory computer-readable medium or media comprising one or more sets of instructions which, when executed by at least one of the one or more processors, causes steps to be performed comprising:
extracting data from a plurality of sources by applying a set of one or more rules correlated to at least some of the sources from the plurality of sources by performing one or more steps comprising:
applying a template that is source specific for extracting data from the source, wherein the template is source specific by being matched to a data format for a website, webpage, datastore, or device, or is matched to one or more Application Programming Interfaces (APIs) for a website, webpage, datastore, or device;
applying one or more keywords from a list of keywords to identify corresponding data in the source; and
applying a learned model to the source, wherein the set of one or more rules represent the learned model;
using at least some of the extracted data to generate records;
assigning one or more labels to each record based upon a category associated with the record or corresponding to at least some of the data contained in the record to obtain labeled records;
identifying one or more entities within each labeled record by applying to a labeled record one or more techniques correlating to that label for identifying an entity or entities;
generating, from the labeled records, entity features and relationships between two or more entities by correlating data from the labeled records that are related to the two or more entities that are identified in labeled records;
for each entity of a set of entities identified in the labeled records, using (1) matrix manipulation on a matrix that represents entity features and relationships between two or more entities, (2) a machine learning model that receives one or more entity features that are related with one or more features of one or more other entities and outputs the vectorized representation of the entity features and relationships, or (3) both to convert the entity features and relationships between two or more entities into the vectorized representation of the entity;
using vectorized representations of entities and resource data to train a set of models using a first set of data;
evaluating each trained model of the set of models using an evaluation set of data; and
selecting a trained model from the set of models based on evaluations.

17. The system of claim 16, further comprising retraining the selected trained model.

18. The system of claim 16, wherein the step of extracting the data further comprises:
assessing a reliability factor for a source; and
in response to determining a low reliability factor for the source, excluding data from that source to improve data reliability.

19. The system of claim 16, wherein the step of generating entity features and relationships comprises combining data from at least two of the plurality of sources.

20. The system of claim 16, wherein the step of generating entity features and relationships comprises at least one of correlating or aligning data from two or more of the plurality of sources.

* * * * *